United States Patent
Keeney et al.

(10) Patent No.: US 8,669,209 B2
(45) Date of Patent: Mar. 11, 2014

(54) PROCESS FOR PREPARING SOLUBLE GRANULES OF SALTS OF PYRIDINE CONTAINING CARBOXYLIC ACIDS

(75) Inventors: Franklin N. Keeney, Carmel, IN (US); Neil A. Foster, Souffelweyersheim (FR); Martin C. Logan, Indianapolis, IN (US); Maria G. Perry, Jamestown, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 167 days.

(21) Appl. No.: 12/951,100

(22) Filed: Nov. 22, 2010

(65) Prior Publication Data

US 2011/0124506 A1    May 26, 2011

Related U.S. Application Data

(60) Provisional application No. 61/263,431, filed on Nov. 23, 2009.

(51) Int. Cl.

| | |
|---|---|
| A01N 43/40 | (2006.01) |
| C07D 211/72 | (2006.01) |
| C07D 211/84 | (2006.01) |
| C07D 213/68 | (2006.01) |
| C07D 213/72 | (2006.01) |
| C07D 213/78 | (2006.01) |
| C07C 61/08 | (2006.01) |
| C07C 59/56 | (2006.01) |
| C07C 59/88 | (2006.01) |
| C07C 65/00 | (2006.01) |
| C07C 229/00 | (2006.01) |
| C07C 62/00 | (2006.01) |

(52) U.S. Cl.
USPC ........... 504/244; 504/254; 504/255; 504/260; 514/345; 514/349; 514/352; 514/354; 546/290; 546/297; 546/298; 546/301; 546/302; 546/304; 546/310; 546/311; 546/312; 546/326; 562/400; 562/405; 562/433; 562/456; 562/458; 562/465; 562/471; 562/472; 562/473; 562/493

(58) Field of Classification Search
USPC .......... 504/244, 254, 255, 260; 514/345, 349, 514/352, 354; 546/290, 297, 298, 301, 302, 546/304, 310, 311, 312, 326; 562/400, 405, 562/433, 456, 458, 465, 471, 472, 473, 493
See application file for complete search history.

(56) References Cited

U.S. PATENT DOCUMENTS

| 3,317,549 | A | * | 5/1967 | Johnston | 546/286 |
| 2005/0215434 | A1 | * | 9/2005 | Ruiz et al. | 504/323 |

FOREIGN PATENT DOCUMENTS

| CA | 1 293 974 C | | 1/1992 | | |
| CA | 1293974 | * | 1/1992 | ............ | C07C 69/736 |
| EP | 1 886 563 A1 | | 2/2008 | | |
| FR | 2 285 071 A1 | | 4/1976 | | |
| WO | 94/28712 A1 | | 12/1994 | | |
| WO | WO94/28715 A1 | * | 12/1994 | ............ | A01N 25/12 |
| WO | 2007/147208 A1 | | 12/2007 | | |
| WO | 2011/063312 | | 5/2011 | | |

* cited by examiner

Primary Examiner — Jane C Osweck
(74) Attorney, Agent, or Firm — Robert Chang; Craig E. Mixan

(57) ABSTRACT

Soluble granule formulations of amine salts of pyridine containing carboxylic acids with improved handling properties are provided by an improved process in which the pyridine containing carboxylic acid is partially neutralized with an amine.

12 Claims, No Drawings

PROCESS FOR PREPARING SOLUBLE GRANULES OF SALTS OF PYRIDINE CONTAINING CARBOXYLIC ACIDS

This application claims the benefit of U.S. Provisional Application Ser. No. 61/263,431 filed on 23 Nov. 2009. The present invention describes an improved process for preparing soluble granule (SG) formulations of amine salts of pyridine containing carboxylic acids with improved processing and handling characteristics.

FIELD OF THE INVENTION

Background of the Invention

Salts of herbicidal carboxylic acids are typically formulated as water based soluble liquids (SL) whereby the salt is dissolved in an aqueous medium, optionally with additional adjuvant or surfactant, for further dilution in the spray tank. These formulations although simple to prepare are typically low in concentration in order to maintain the active herbicidal ingredient in solution at low ambient temperatures. This need for a relatively low active ingredient concentration increases the volume of the commercial packaging required, the disposal costs of the contaminated packaging after use and the cost of transportation of the formulation.

A more efficient method of handling these types of active ingredients is to prepare a dry solid formulation, such as a soluble granule (SG), whereby an aqueous solution of the active ingredient salt is dehydrated to provide the product as a solid normally in the form of a granule. The dehydration and granulation processes used can vary depending on the physical and chemical stability of the organic salt.

Granular formulations such as soluble granules or water dispersible granules (WG) are becoming more commonly used in agricultural today because of their relative safety compared to liquid formulations and the advantages they offer with regard to cost savings in packaging and transportation. Granule formulations can be produced using one of the following processing methods: (1) pan granulation, (2) mixing agglomeration, (3) extrusion granulation, (4) fluid bed granulation or (5) spray drying granulation. The physicochemical properties of the active ingredient and additives are important to consider when choosing a process to use. G. A. Bell and D. A. Knowles in, "Chemistry and Technology of Agrochemical Formulations," D. A. Knowles, editor, (Kluwer Academic Publishers, 1998), pages 41-114, describe the types of granules used in agricultural chemical formulations and provide many references to the production of these solid formulations.

Granules can sometimes be difficult to produce owing to the physical properties or stabilities of the materials to be processed. Salts of herbicidal pyridine containing carboxylic acids prepared by neutralizing the carboxylic acid function with an amine or hydroxide base can sometimes possess low melting points which may make them unsuitable for processing into high quality granules. The physical properties of these salts may also be dependent on the experimental conditions used in their preparation such as the relative amounts of base and pyridine containing carboxylic acid used in the preparation, how the two components are mixed together, the temperature during preparation and the amount of solvent used. In such cases, granules may be produced that are sticky, making processing difficult and resulting in granules that, after final processing and drying, may cake together, flow poorly or may produce excessive dust. The present invention provides an improved process of making high quality, soluble granules of amine salts of herbicidal pyridine containing carboxylic acids with improved handling properties that may otherwise be difficult to process.

SUMMARY OF THE PRESENT INVENTION

The present invention concerns an improved process for preparing solid formulations of amine salts of herbicidal pyridine containing carboxylic acids with improved handling properties which comprises:
 a) mixing the herbicidal pyridine containing carboxylic acid with an amine and water to form a dispersed solid or solution;
 b) removing the water from the dispersed solid or solution to provide a solid; and
 c) processing the solid into granules;
wherein the improvement comprises using less than one molar equivalent of the amine with respect to the herbicidal pyridine containing carboxylic acid.

The present invention provides an improved process for producing soluble granules of amine salts of herbicidal pyridine containing carboxylic acids that are non-sticky and, after drying, are easy to size, free-flowing, non-caking and dust free. The soluble granules are readily dissolved in water and optionally diluted in an aqueous spray mixture for use in weed management.

DETAILED DESCRIPTION OF THE PRESENT INVENTION

The present invention provides an improved process for making soluble granules of amine salts of herbicidal pyridine containing carboxylic acids that can be difficult to make because of the physical properties of the composition. By using partial neutralization of the herbicidal pyridine containing carboxylic acid with an amine base, the resulting partially neutralized salt of the herbicidal pyridine containing carboxylic acid has a higher melting point than the fully neutralized pyridine containing carboxylic acid thereby providing a material with improved physical properties and processing characteristics for conversion into granular formulations. The improved process produces soluble granules that are non-sticky during processing and, after final drying and processing, are free-flowing, non-caking and dust free.

The amines used in the present invention are primary, secondary or tertiary alkylamines, alkanolamines, alkylalkanolamines or alkoxyalkanolamines wherein the alkyl and alkanol groups are saturated and contain from $C_1$-$C_4$ alkyl groups individually. Examples of preferred amines include monoethanolamine, diethanolamine, triethanolamine, dimethylethanolamine, dimethylethylamine and triethylamine.

Pyridine containing carboxylic acids of the present invention include picolinic acids such as aminopyralid, clopyralid and picloram and pyridinyloxyacetic acids, such as triclopyr and fluroxypyr.

The partially neutralized amine salts of the pyridine containing carboxylic acids of the present invention are formed by mixing the herbicidal pyridine containing carboxylic acid with less than one molar equivalent of the amine in the presence of water. The minimum amount of water required in the process will depend on what is needed to achieve adequate mixing of the components in order to completely form the partially neutralized salt of the pyridine containing carboxylic acid. The maximum amount of water that can be used in the process will generally depend on what is practical and economical for the process. The partially neutralized salt of the pyridine containing carboxylic acid comprises a mixture of the salt of the pyridine containing carboxylic acid (the salt) and the pyridine containing carboxylic acid (the free acid), wherein the salt is generally present in greater amounts than the free acid. Typically, 70 mole per cent or more of the salt is formed on a molar basis with respect to the total amount of the salt and the free acid present in the partially neutralized salt of the pyridine containing carboxylic acid. The amount of the amine used to make the partially neutralized salt of the pyridine containing carboxylic acid may range from 0.70 to 0.99, preferably from 0.85 to 0.99, on a molar basis compared to the starting amount of the pyridine containing carboxylic acid.

The pyridine containing carboxylic acids may range in assay from about 80 to about 99% and may contain impurities remaining from the manufacturing process such as inorganic acids, inorganic salts and reaction side-products, and water. These impurities may have an effect on: (1) the partial neutralization of the pyridinecarboxylic acid by requiring additional amine to be used than would normally be expected on a theoretical basis, such as when an inorganic acid impurity is present, or (2) the quality of granules produced.

The preparation of the partially neutralized amine salt of the pyridine containing carboxylic acid can be effectively conducted by measuring the pH of the mixture or solution of the pyridine containing carboxylic acids as the amine is added. The initial pH of the starting mixture or solution of the pyridine containing carboxylic acid in water is dependent on the pKa, or the negative log of the acid dissociation constant, of the pyridine containing carboxylic acid used. For picolinic acids of the present invention, the starting pH will be from about 1.5 to about 3.5 pH units, and for pyridinyloxyacetic acids of the present invention the starting pH will be from about 3.5 to about 5.5 pH units. These pH ranges may extend lower if acidic impurities are present. The addition of the amine to the mixture or solution of the picolinic acid in water may be stopped when the pH reaches a value of between about 4 to about 6 pH units, and the addition of the amine to the mixture or solution of the pyridinyloxyacetic acid in water may be stopped when the pH reaches a value of between about 5.5 to about 7.0 pH units to provide the mixture or solution of the respective partially neutralized salts of the pyridine containing carboxylic acids.

Alternatively, the partially neutralized amine salt of the pyridine containing carboxylic acid can be prepared by adding the pyridine containing carboxylic acid as a dry solid or a wetcake, i.e., a solid containing water, to an aqueous solution or neat liquid of the amine. The pH of the resulting mixture or solution prepared by this alternative method can then be adjusted higher or lower by adding more of the amine or the pyridine containing carboxylic acid, respectively, to reach the desired pH level of the final mixture or solution. This alternative method allows for the use of less water in the process, which can lead to improved drying efficiency and cost savings.

The partially neutralized amine salt of the herbicidal pyridine containing carboxylic acid has a higher melting point than the fully neutralized or over neutralized pyridine containing carboxylic acid thereby providing a material with improved physical properties and processing characteristics for conversion into granular formulations. The partially neutralized salt formed by combining clopyralid with less than one molar equivalent of monoethanolamine has a higher melting point (108° C. melting point as measured by differential scanning calorimetry) than does the fully neutralized salt of clopyralid monoethanolamine (103° C. melting point as measured by differential scanning calorimetry) which is formed by combining clopyralid with one or more than one molar equivalents of monoethanolamine. The higher melting, partially neutralized monoethanolamine salt of clopyralid, after further processing, forms granules that are non-sticky during processing and are free-flowing and non-caking after final drying. The lower melting, fully neutralized monoethanolamine salt of clopyralid, after further processing, forms granules that are sticky during processing and are not free-flowing, but generally cake together after final drying.

The composition used in the present invention comprises, on a dry weight basis relative to the total composition, 40-99.9% of the partially neutralized salt of the herbicidal pyridine containing carboxylic acid and 0.1-60% of inert ingredients. The inert ingredients may comprise impurities remaining from the manufacturing process of the herbicidal pyridine containing carboxylic acid, added formulation ingredients or water.

The improved process of the present invention comprises the steps of forming the partially neutralized amine salt of the pyridine containing carboxylic acid as a dispersed solid or solution in water, optionally adding inert formulation ingredients to the dispersed solid or solution in water and then removing the water by drying the dispersed solid or solution in water, optionally containing inert formulation ingredients, to provide the product of the present invention, either directly or after further processing, as soluble granules. The soluble granules of the present invention are free-flowing, non-caking, dust free and readily soluble in water.

The dispersed solid or solution of the partially neutralized amine salt of the pyridine containing carboxylic acid in water may optionally be mixed with from about 0.1 to 60 weight per cent, on a dry weight basis relative to the total composition, of inert formulation ingredients such as, but not limited to, dispersants, wetting agents, binding agents, antifoaming agents, disintegrating agents, stabilizing agents and carriers to aid in the formation and stability of the final soluble granules of the present invention and improve their dispersion and solubility in water.

The dispersed solid or solution of the partially neutralized amine salt of the pyridine containing carboxylic acid in water, optionally containing inert formulation ingredients, is then dried at a temperature that is at least 20 to 30° C. below the melting point of the respective amine salt of the pyridine containing carboxylic acid to provide the product of the current invention either directly or after further processing. The drying may be done with a rotary dryer to furnish a solid material for further processing or by other drying methods such as spray drying, drum drying, conveyor drying or other drying methods known to those skilled in the art. The drying step in the process may optionally be combined with a granulation or agglomeration step, for example with spray drying or fluid-bed drying, to provide, after any necessary final processing, the soluble granule product of the current invention. These and other drying methods and the equipment used are discussed by P. Y. McCormick in "Drying," in volume 8 of the Kirk-Othmer Encyclopedia of Chemical Technology (John Wiley and Sons, 1993), pages 475-519.

The solid material produced by drying the dispersed solid or solution of the partially neutralized amine salt of the pyridine containing carboxylic acid in water, optionally containing inert formulation ingredients, may optionally be milled or passed thru a sieve to provide a powder that is of uniform particle size and suitable for further processing into granules.

Granulation methods that may be used in the current invention may include, but are not limited to, drum, disk, pan or spray-drying agglomeration, fluid-bed granulation, basket extrusion, twin dome extrusion and high pressure extrusion with a single screw or a twin screw extruder. These and other granulation processing methods and the equipment used in them are described by C. E. Capes and K. Darcovich in "Size Enlargement," in volume 22 of the Kirk-Othmer Encyclopedia of Chemical Technology (John Wiley and Sons, 1997), pages 222-255.

For granulation by extrusion, the powder of the milled or sieved partially neutralized salt of the pyridine containing carboxylic acid is treated with water and mixed well to provide a kneadable wet cake. The exact amount of water used to form the kneadable wet cake may vary with respect to the particular composition used or the method of granulation chosen and may affect the quality of the granules produced such as whether they stick together after being formed or cake together after final drying.

The kneadable wet cake may be processed into granules by extrusion through a basket die at low pressure and near ambient temperature to produce wet granules. The die may have openings of 0.5 to 5 mm and preferably have openings of 0.6 to 2 mm. The size of the die openings will depend on the performance properties needed from the granules such as how quickly they wet, disperse and dissolve in the water of a spray solution. The wet granules may be partially dried with a stream of ambient temperature air as they emerge from the extruder to minimize or prevent the granules from clumping or sticking together as they form. The partially dried granules are further dried at 50 to 90° C., preferably at 60 to 80° C., to produce dry granules with a water content of less than 2 weight per cent non-molecularly bound water relative to the total weight of the granules.

The dried granules may be sized to a predetermined length by using, for example, an oscillating cutter or other sizing device or method known in the art. The sized granules may be sieved to provide a predetermined size range of granules as the finished product. The sieving process may remove granules that are too large or too small relative to the predetermined size range of granules. The granules or solids that are outside the predetermined size range may be recycled back into the process and used to make additional granules.

The soluble granules of the present invention contain 40-99.9 weight per cent of the partially neutralized salt of the herbicidal pyridine containing carboxylic acid and are free-flowing, non-caking, dust free and readily soluble in water.

In an preferred example of the present invention, an aqueous dispersion of clopyralid can be partially neutralized with about 0.97 equivalents of monoethanolamine until a pH of about 5.5 is reached, water can be removed by rotorary evaporation and the solid can be processed into granules by extrusion.

The following examples illustrate the present invention.

Example 1

Preparation of Soluble Granules of Clopyralid Ethanolamine

A mixture made from mixing 3,448 grams (g) of clopyralid (dry weight basis) as a dry solid or wetcake and 5.1 liters (L) of water was stirred and neutralized with 1,060 g of monoethanolamine at room temperature. Additional monoethanolamine was added as needed until a pH of approximately 5.5 was reached at a temperature of 22° C. to provide the partially neutralized monoethanolamine salt of clopyralid as a clear solution. The solution was filtered through a coarse fritted filter to remove a few insoluble particulates and the water was then removed by rotorary evaporation at 75° C. to provide a solid of the partially neutralized clopyralid monoethanolamine salt. The solid was passed through a 20 mesh sieve to breakup any lumps that formed during drying. The sieved solid was treated with water to achieve a moisture content of about 5.0-5.5 weight per cent relative to the total weight of the solid and a kneadable wet cake was formed after stirring the solid and water together. The kneadable wet cake was fed into a NICA™ E-140 low pressure extruder (GEA Pharma Systems) fitted with a 1.0 millimeter (mm) die to produce granules. The inlet and outlet port temperatures during extrusion were near ambient temperature. The granules were partially dried with a stream of ambient temperature air as they emerged from the extruder and were further dried in an oven at 50-60° C. to provide dry granules with a water content of 0.20-0.25 weight per cent. The dry granules were sieved through a 16 inch (40.64 centimeters) Sweco sieve with 10 mesh and 30 mesh screens installed to provide a finished cut of granules that had a particle size range of between 600 and 2000 microns (μm). A chemical assay of the dried granules indicated an active ingredient concentration of 97.2 weight per cent and a water content of 0.20 weight per cent, with respect to the total weight of the granules.

Example 2

Preparation of Partially Neutralized Clopyralid Ethanolamine

To a stirred sample of 750 grams of neat monoethanolamine at 60° C. was added 2822 grams of a wetcake of clopyralid (75% clopyralid, 21% water). After stirring for 30 minutes after completing the clopyralid addition, the pH of the resulting mixture was measured and adjusted to a final pH value of 5.35-5.65 by adding an additional 135 grams of clopyralid to the mixture. The aqueous mixture containing the partially neutralized monoethanolamine salt of clopyralid was then allowed to cool and solidify. The solid was placed in a fluid bed dryer and dried at 70-75° C. to produce the solid, partially neutralized monoethanolamine salt of clopyralid with a water content of less than 0.5%.

What is claimed:

1. An improved process for preparing solid formulations of amine salts of herbicidal pyridine containing carboxylic acids with improved handling properties comprising:
   a) mixing the herbicidal pyridine containing carboxylic acid with an amine and water to form a dispersed solid or solution;
   b) removing water from the dispersed solid or solution to provide a solid; and
   c) processing the solid into granules;
wherein the improvement comprises using less than one molar equivalent of the amine with respect to the herbicidal pyridine containing carboxylic acid.

2. The process of claim 1 wherein the herbicidal pyridine containing carboxylic acid is clopyralid and the amine is monoethanolamine.

3. The process of claim 2 wherein the mixing of step a comprises adding monoethanolamine to an aqueous dispersion of clopyralid until the pH reaches a value of about 5 to 6.

4. The process of claim 2 wherein the mixing of step a comprises adding solid clopyralid to monoethanolamine until the pH reaches a value of about 5 to 6.

5. The process of claim 2, wherein 0.97 equivalents of monoethanolamine are mixed.

6. The process of claim 3, wherein the processing the solid into granules comprises extrusion.

7. The process of claim 4, wherein the processing the solid into granules comprises extrusion.

8. The process of claim 1, wherein the herbicidal pyridine containing carboxylic acid is a picolinic acid or pyridinyloxyacetic acid.

9. The process of claim 8, wherein the herbicidal pyridine containing carboxylic acid is aminopyralid, clopyralid, picloram, triclopyr, or fluroxypyr.

10. The process of claim 9, wherein the amine is monoethanolamine, diethanolamine, triethanolamine, dimethylethanolamine, dimethylethylamine, or triethylamine.

11. The process of claim 10, wherein the mixing of step a comprises adding the amine to the herbicidal pyridine containing carboxylic acid until the pH reaches a value of about 5 to 6.

12. The process of claim 11, wherein the processing the solid into granules comprises extrusion.

* * * * *